(12) United States Patent
Vetter et al.

(10) Patent No.: US 12,336,696 B2
(45) Date of Patent: *Jun. 24, 2025

(54) DEVICES AND METHODS FOR PORTABLE, ADJUNCTIVE VACUUM SOURCE AND CYTOLOGY/HISTOLOGY COLLECTION SYSTEMS FOR BIOPSY DEVICES

(71) Applicant: TransMed7, LLC, Portola Valley, CA (US)

(72) Inventors: Paul A Vetter, Portola Valley, CA (US); Eugene H Vetter, Portola Valley, CA (US); Robert D Sauchyn, Regina (CA); James W Vetter, Portola Valley, CA (US)

(73) Assignee: Transmed7 LLC, Portola Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/387,387

(22) Filed: Nov. 6, 2023

(65) Prior Publication Data
US 2024/0173020 A1      May 30, 2024

Related U.S. Application Data

(63) Continuation of application No. 17/480,588, filed on Sep. 21, 2021, now Pat. No. 11,844,501, which is a
(Continued)

(51) Int. Cl.
*A61B 10/02*          (2006.01)

(52) U.S. Cl.
CPC ...... *A61B 10/0283* (2013.01); *A61B 10/0275* (2013.01); *A61B 2560/0214* (2013.01); *A61B 2560/0431* (2013.01)

(58) Field of Classification Search
None
See application file for complete search history.

(56) References Cited

U.S. PATENT DOCUMENTS

| 3,330,268 A | 7/1967 | Goldsmith |
| 9,956,326 B2 * | 5/2018 | Ramella ................. A61M 1/60 |

(Continued)

FOREIGN PATENT DOCUMENTS

| WO | 8907911 A1 | 9/1989 |
| WO | 03053346 A2 | 7/2003 |

OTHER PUBLICATIONS

Communication pursuant to Article 94(3) EPC in EP Application 20790180.2 dated Jan. 22, 2024 (4 pages).

*Primary Examiner* — May A Abouelela
*Assistant Examiner* — Samuel C Kim
(74) *Attorney, Agent, or Firm* — YOUNG LAW FIRM, P.C.

(57) ABSTRACT

A universal, self-contained, self-powered, compact, external vacuum source and cytology or cytology and histology collection, storage, preservation and transport system device may be configured to couple to any suitable generic biopsy or interventional device. Embodiments may comprise structures and functionality for the addition of such a portable, compact, self-contained, self-powered, universal vacuum and cytology/histology collection module to biopsy or interventional devices. Embodiments may be portable, disposable or reusable and may be electrically, mechanically and/or manually powered and operated. Embodiments may additionally provide structures and functionality for use with other vacuum and/or cytology or histology collection systems to which this system may itself be attached.

23 Claims, 8 Drawing Sheets

Related U.S. Application Data continuation of application No. 16/389,767, filed on Apr. 19, 2019, now Pat. No. 11,234,684.

(56) References Cited

U.S. PATENT DOCUMENTS

| | | |
|---|---|---|
| 11,234,684 B2 * | 2/2022 | Vetter ................ A61B 10/0283 |
| 11,844,501 B2 * | 12/2023 | Vetter ................ A61B 10/0283 |
| 2003/0035759 A1 | 2/2003 | Coyne |
| 2007/0191731 A1 | 8/2007 | Kaye |
| 2010/0042015 A1 | 2/2010 | Brown |
| 2013/0053724 A1 * | 2/2013 | Fiebig ................ A61B 10/0266 |
| | | 600/567 |
| 2015/0290411 A1 | 10/2015 | Warrington et al. |

* cited by examiner

DEVICES AND METHODS FOR PORTABLE, ADJUNCTIVE VACUUM SOURCE AND CYTOLOGY/HISTOLOGY COLLECTION SYSTEMS FOR BIOPSY DEVICES

BACKGROUND

There is a need for portable, adjunctive, universally adaptable, self-contained, internally or self-powered and compact vacuum and cytology collection systems for soft and hard tissue biopsy and other interventional medical devices.

SUMMARY

A universal external vacuum source with an integrated cytology or cytology and histology collection system described herein, according to embodiments described herein, may be adapted and attached directly to a generic biopsy device to provide vacuum to such a device in order to enhance such generic biopsy device's performance characteristics for collection and internal transport of tissue specimens obtained by the biopsy device, while at the same time collecting cytology (liquids and loose cells or tissue fragments) collected from the target tissue being biopsied, for direct pathologic characterization and correlation to the histologic specimens (solid tissue obtained from a target lesion or tissue site) obtained by the biopsy device to which such a universal vacuum and cytology collection system may be attached. According to additional embodiments, a universal external vacuum source and cytology collection system device may also incorporate additional elements such as a universal, filtered solid tissue specimen collection magazine or vessel, in which embodiments the external vacuum and cytology collection system may also be considered a universal, self-contained, self-powered external vacuum source and cytology and histology collection, storage and transport system, which may also be adapted and attached directly to a generic biopsy device to provide vacuum to such a device as well as capture both cytology and histology from such a generic biopsy device. Embodiments are drawn to medical devices and methods that are used for provision of vacuum and cytology collection for tissue biopsy and interventional medical devices. Embodiments may comprise structures and functionality for the addition of a portable, compact, universal vacuum and cytology collection module to biopsy or interventional devices. Embodiments may be portable, disposable or reusable and may be electrically, mechanically and/or manually powered and operated. Furthermore, embodiments may also provide structures and functionality for use with other vacuum and/or cytology or histology (solid tissue) collection systems to which this system may itself be attached.

DETAILED DESCRIPTION

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations. Indeed, although the figures are variously described as showing "an embodiment" or characterized as being "according to embodiments", all of the structures and associated functionalities may be present in a single device or one or more of the structures and associated functionalities may be omitted from one device or present in another device. Alternatively, some of the structures and functionalities shown and described herein may be included in some devices according to one or more embodiments, while other structures and functionalities shown and described herein may be included in in or more other devices according to embodiments. Similarly, the acts or steps shown and described herein may form a single embodiment of a single method or some acts or steps may be added or omitted in other sequences to form one or more embodiments of one or more other disclosed methods.

The vacuum and cytology collection device disclosed herein is configured and functions as a source of vacuum and cytology or liquid collection apparatus in conjunction with a biopsy device or other interventional device as may be used for tissue and/or cytology collection to appropriately and accurately characterize and capture tissue and liquids for subsequent pathologic analysis, according to various methods and embodiments. As such, the vacuum and cytology collection device described herein is compatible with a variety of generic tissue collection devices.

Reference will now be made in detail to the construction and operation of embodiments illustrated in the accompanying drawings.

Figure 1:
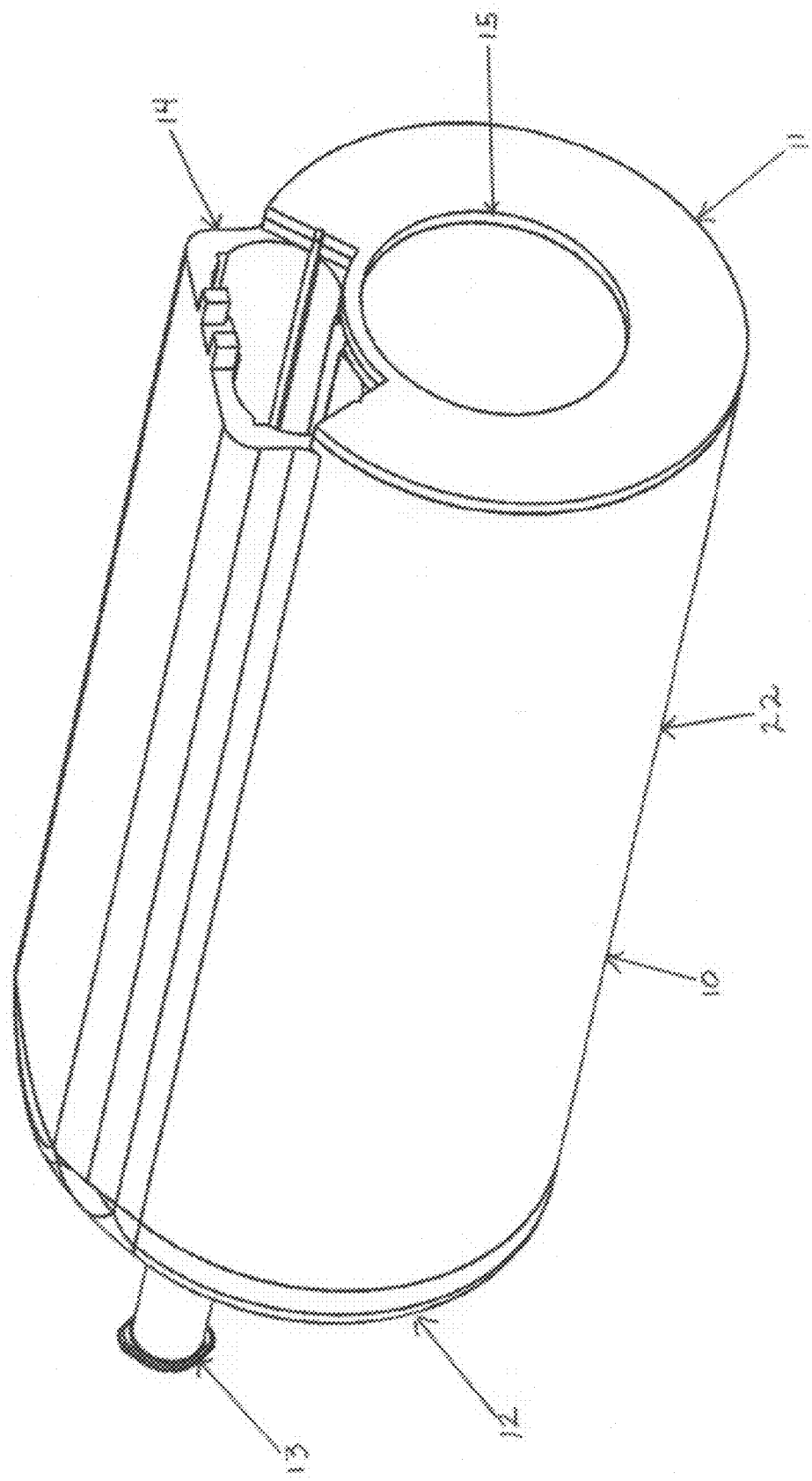
FIG. 1 is an angled side view of a vacuum and cytology collection device 10 according to one embodiment.

FIG. 1 is an angled side view of a vacuum and cytology collection device 10 according to one embodiment. As shown, device 10 may comprise a front plate element 11, a rear plate element 12, an external evacuation port 13, a battery and vacuum pump compartment 14, a generic specimen chamber aperture element 15 and a main body element 22. Device 10 is a self-contained, portable, adaptable, self-powered vacuum and cytology collection system, which may itself be variously adapted to fit any of a variety of generic biopsy or interventional medical devices to which it may be attached. Herein, the phrase "generic biopsy device" and variants thereof is used to convey that the present vacuum, cytology and/or histology collection device may be readily adapted to be coupled to most any biopsy or interventional device from any manufacturer. As such, the present device is a universal vacuum and cytology collection device.

Figure 2:
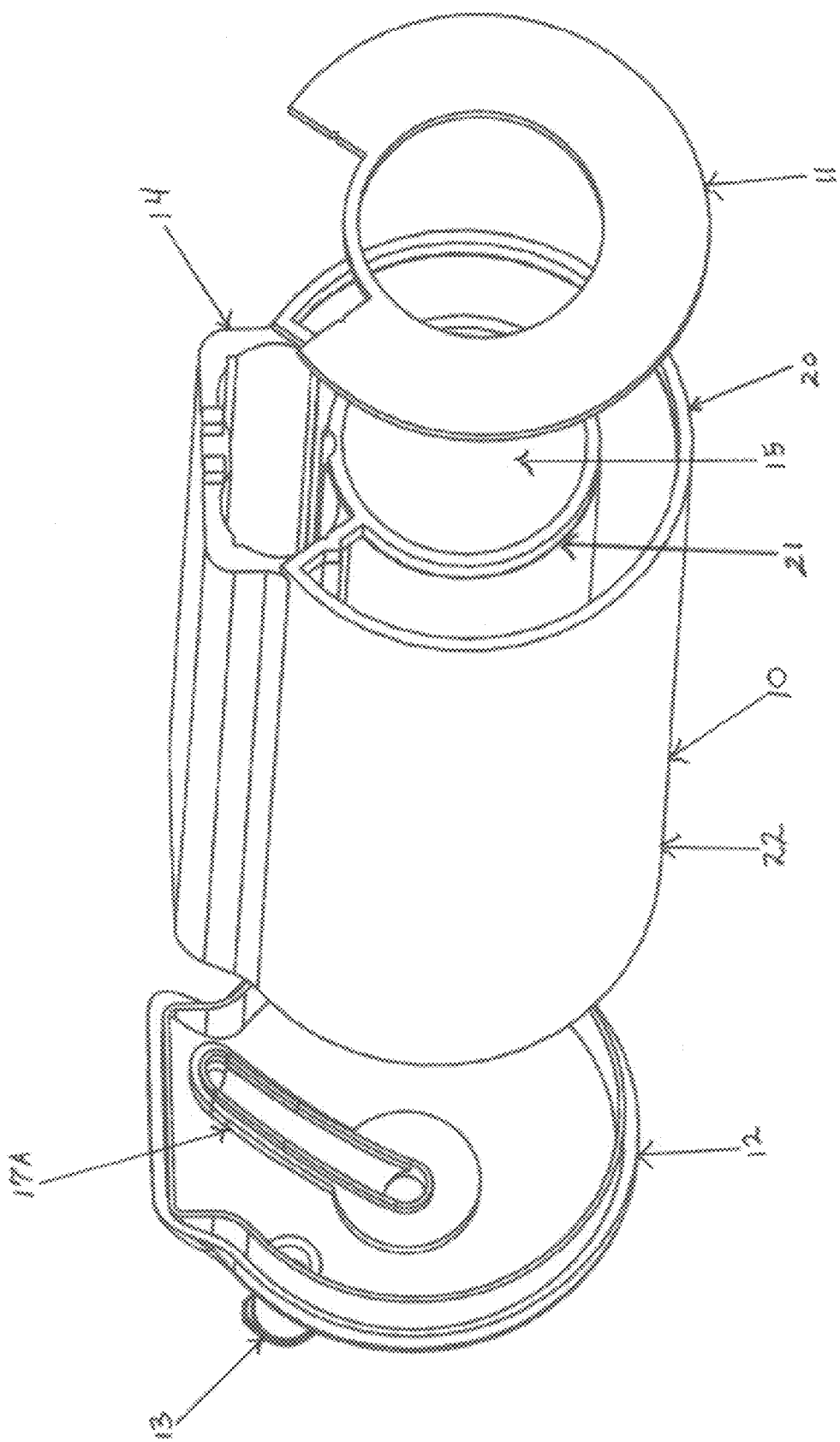
FIG. 2 is a perspective angled and exploded side view of main structural components of a vacuum and cytology collection device 10, according to one embodiment.

FIG. 2 is a perspective angled and exploded side view of the main structural components of the vacuum and cytology collection device 10, according to one embodiment. In this illustration, device 10's main structural elements may include the main, outer body element 22 having a co-axially-disposed inner wall 21 and an outer wall 20, the battery and pump compartment 14 and aperture 15; the rear plate element 12 with its external exhaust port 13 and a half channel 17A; and the front plate 11. The inner wall 21 is an outer surface of an inner tubular element co-axially-disposed within the tubular main body element. The following illustrations will more specifically describe these elements, according to various embodiments.

Figure 3:
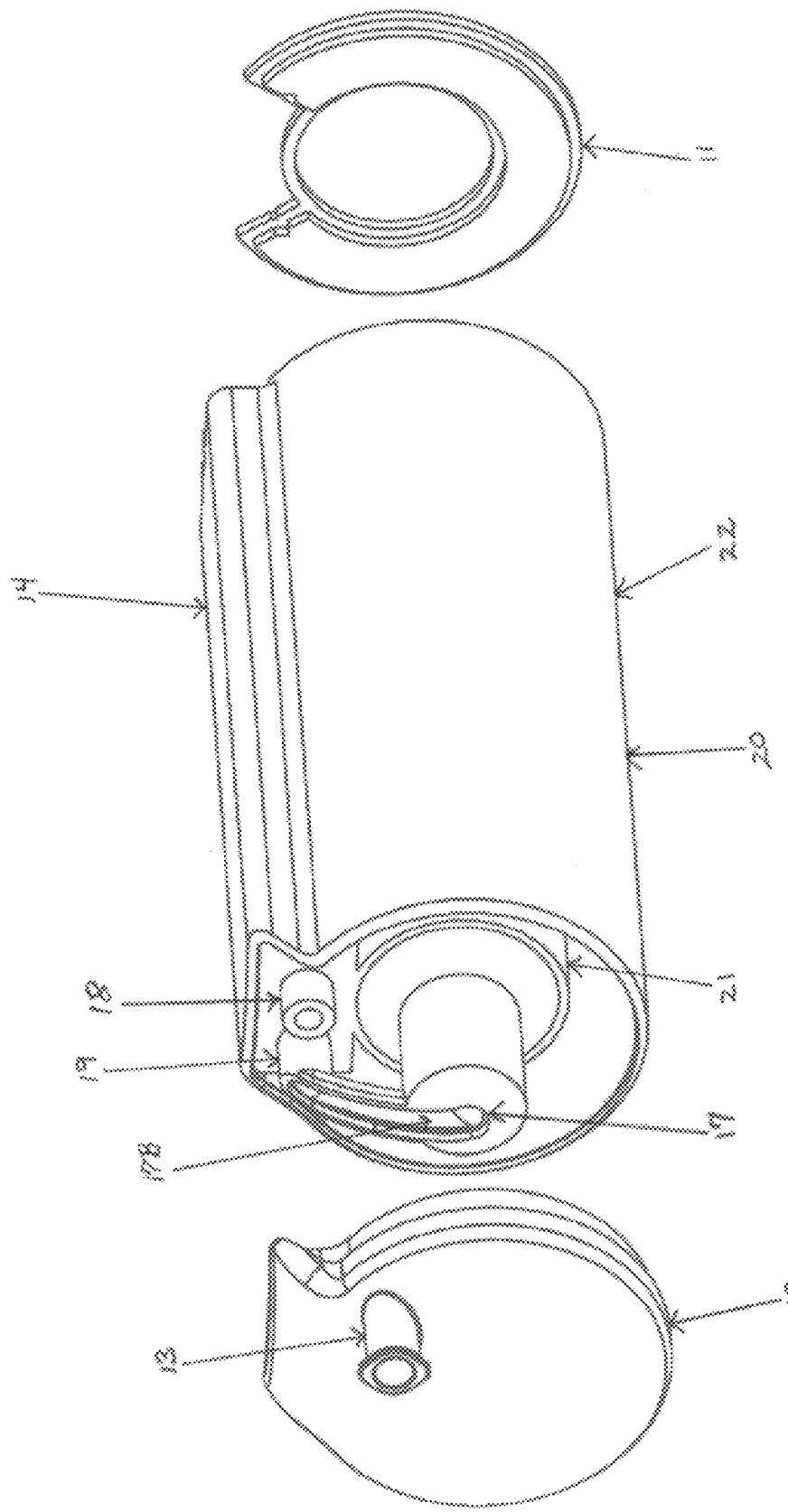
FIG. 3 is a perspective angled and exploded side view of main structural components of a vacuum and cytology collection device 10, according to one embodiment.

FIG. 3 is a perspective angled and exploded side view of main structural components of a vacuum and cytology collection device 10, according to one embodiment. In this view, the rear plate element 12, with its external evacuation port 13 may be seen separated from the main body element 22. Rear plate element 12 is configured to seal against the rear surface of the outer wall 20 of the main body element 22, in such a manner as to allow vacuum to be drawn from an internal vacuum pump, (not shown in this figure) located at the rear of the battery and vacuum pump compartment 14, through vacuum port 19 and vacuum channel port 17, with its half channel 17B illustrated in this figure, to a vacuum connection that may be integral with inner wall 21 of main body element 22. Front plate element 11 is configured to seal against both the outer wall 20 and inner wall 21 of main body element 22 to form a vacuum and liquid tight seal facing between the inner and outer walls of main body element 22. Outer wall 20 of main body element 22, in conjunction with inner wall 21 thus forms a fluid and tissue collection chamber around device 10's aperture 15, as shown in FIG. 1 above. Not shown in this figure is a corresponding half channel 17A of vacuum channel port 17, which is integral with rear plate 12's inner surface, and as was previously shown in FIG. 2 above. Thus, when the rear plate 12 is sealed against the main body element 22 of outer wall element 20, the two half channels 17A and 17B will be mated and sealed to form a vacuum and liquid tight vacuum channel port 17 so that vacuum may be imparted from a vacuum pump located in battery and pump compartment 14, through vacuum port 19 allowing suction from vacuum channel port 17 to the intake of the vacuum pump, to a generic biopsy device specimen collection chamber, not shown in this figure. Although not visible in this figure, the main body element 22 may be configured with a short inner extension of the inner wall 21, through which vacuum channel port 17 passes, which short inner extension may be configured with a short internal connection luer or extension in order to mate with the exhaust port of a generic biopsy device's specimen collection chamber according to one embodiment; or alternatively mate with the exhaust port of a generic specimen collection chamber as an integral element structure of device 10, which may itself then mate to a generic biopsy device, according to other embodiments. This inner wall internal connection may be fitted with a tube and connection to vacuum channel port 17 which may then allow for the device 10 to be fitted to virtually any generic biopsy or interventional instrument or device, according to embodiments and methods. As may be envisioned by one skilled in the art, device 10's configuration may readily be adapted by any of a number of methods to a generic biopsy device for purposes of the provision of vacuum and cytology collection capability, as well as histology (solid tissue specimens) collection capability, and all such methods and structures are considered to be within the scope of the present disclosure.

Exhaust port element 18 is located at the rear end of battery and pump compartment 14, and allows liquids drawn through the vacuum pump to be ejected into the fluid and tissue collection chamber formed between inner wall 21 and outer wall 20, when front plate 11 and rear plate 12 are mated and sealed to the main body element 22. It should be noted that external evacuation port 13 of rear plate 12 does not mate directly to the vacuum pump's exhaust port element 18 when the rear plate 12 is mated and sealed to the main body element 22. The vacuum pump's exhaust port element 18 thus delivers liquids and/or gasses directly to the fluid and tissue collection chamber, while external evacuation port 13 serves as a structure for emptying the from the fluid and tissue collection chamber or for connecting to an additional, external vacuum source and cytology collection system, according to embodiments. According to embodiments, the external evacuation port 13 may be fitted with an external luer or press-fit connection to, for example, an external one way valve, a simple valve or a pressure relief valve to allow any air in the fluid and tissue collection chamber of device 10 to escape as liquids may be collected by device 10. A simple tube may also be connected to external evacuation port 13 to allow for cytology collection to an external vacuum source and liquid collection apparatus or vessel in the event that the device 10's fluid and tissue collection chamber's volume is exceeded. External evacuation port 13 may also be used to empty cytology fluids into a container for pathologic examination. The external evacuation port 13 may also be configured to receive a cap seal, according to embodiments. The external evacuation port 13 may also be configured to be fitted with an apparatus for back flushing liquids as may be desired.

Thus, a generic biopsy instrument's specimen collection chamber (not shown in this illustration) which may be placed internally to device 10's aperture 15 as shown in FIG. 1 above, and sealed internally to vacuum channel 17, may be subject to vacuum and liquid collection forces imparted to such a generic biopsy device specimen (collection) chamber by vacuum channel port 17. Alternatively, vacuum channel port 17 may be fitted with an appropriate tube or other connection for connection to the specimen collection chamber of a generic biopsy device. In such manner, even a generic biopsy device that is not originally configured for specimen collection using vacuum assistance may be converted to a vacuum assisted device in conjunction with the use of device 10. Further, once device 10 has collected cytology as a result of its use in conjunction with a generic biopsy or interventional instrument, device 10 may be separated from the generic biopsy device's specimen collection system, and be itself sealed at both rear plate 12 by, for example, a cap placed over external evacuation port 13 of rear plate 12, and internally with an appropriate closing mechanism for vacuum port 17. Liquids that have been captured between inner wall 21 and outer wall 20 of device 10 may thus be transferred along with a generic specimen collection system or simply by carrying the device 10 alone to a pathology laboratory intra-operatively or post-operatively for analysis and direct correlation with any tissue specimens obtained by a generic biopsy or interventional device used in conjunction with device 10. It should also be noted that external evacuation port 13 provides direct access to the cytology or fluid and/or tissue collection chamber of device 10, and thus fixative materials of any nature may be directly added to the collected liquid and cytology postprocedurally in order to preserve the cytology before or after transfer of the liquid thus captured to a pathology laboratory for subsequent analysis, as desired.

Figure 4:
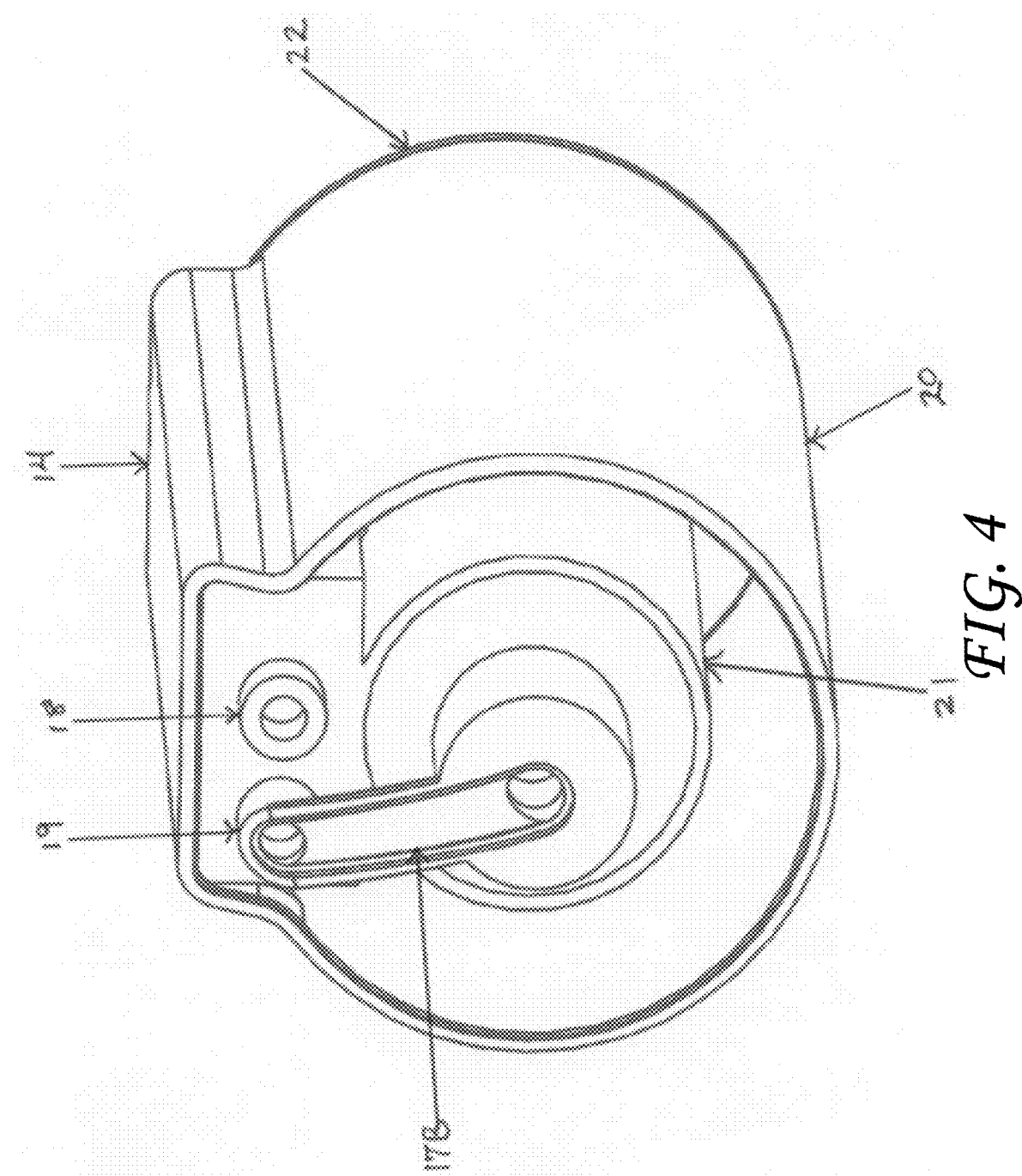
FIG. 4 is an angled rear view of the main body structural element of a vacuum and cytology collection device 10, according to one embodiment.

FIG. 4 is an angled rear view of the main body structural element 22 of a vacuum and cytology collection device 10, according to one embodiment. In this illustration, the inner wall 21 and outer wall 20 may be observed, and the (at least partially toroidal or doughnut-shaped, in one embodiment) space between these walls may serve as the cytology collection chamber of device 10. The volume thus circumscribed for fluid and cytology collection may be approximately 60 cubic centimeters, although it is to be understood that a smaller or larger volume metric of any range may be associated with this cytology collection chamber of device 10, according to embodiments. Also visible in this figure are the battery and pump compartment 14, the vacuum port 19 and exhaust port 18 for the vacuum pump (not shown in this illustration) corresponding to vacuum pump intake and exhaust, respectively, and the half channel 17B which has been previously described.

Figure 5:
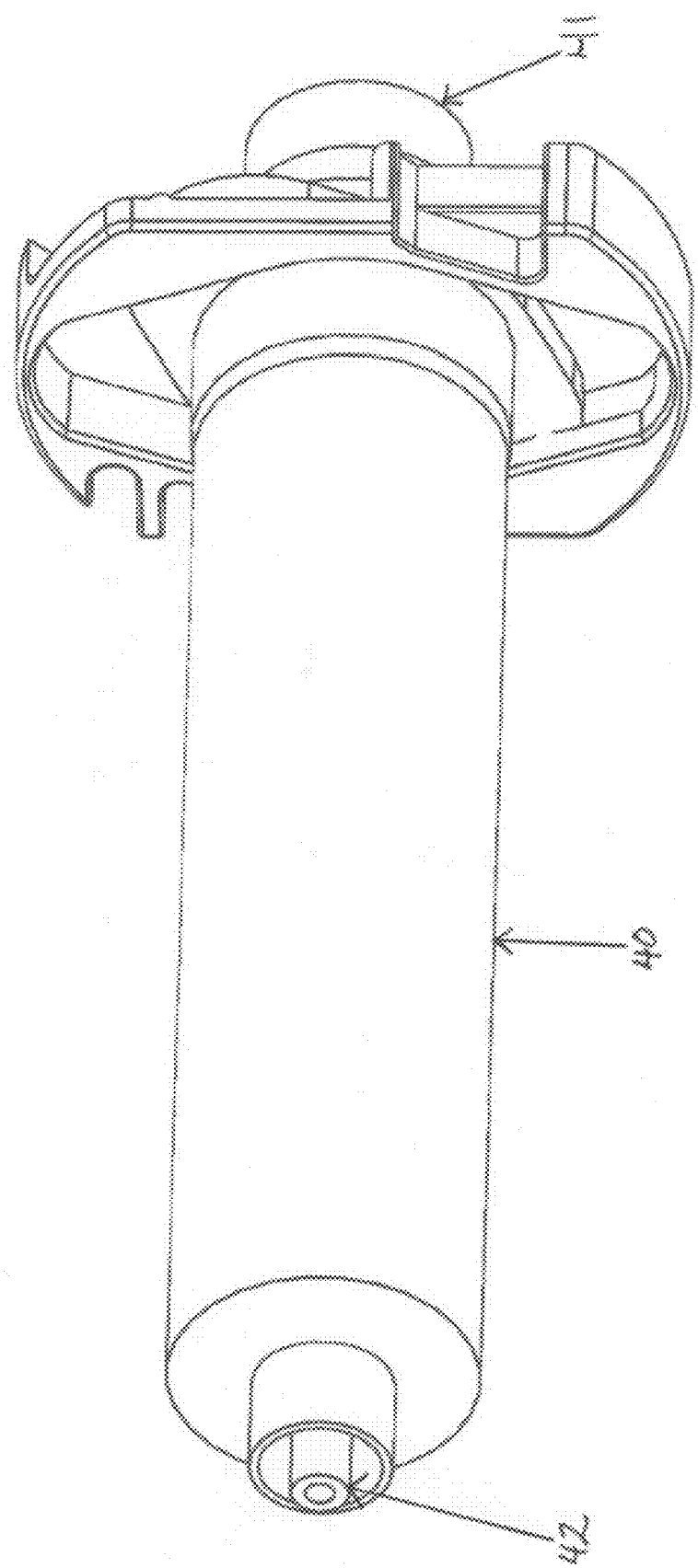
FIG. 5 is an angled side view of a separate generic specimen collection chamber of a separate, generic biopsy device to which a vacuum and cytology collection device 10 may be attached, according to one embodiment.

FIG. 5 is an angled side view of a separate generic specimen collection chamber 40 of a separate, generic biopsy device to which a vacuum and cytology collection device 10 may be attached, according to one embodiment. Although the generic specimen collection chamber thus illustrated in this figure is similar or identical to a syringe body which may be used for such purposes, it is to be understood that generic biopsy and other interventional devices may feature alternate configurations for purposes of specimen collection and preservation. According to one embodiment, the device 10 may be configured to be universally adaptable to a generic biopsy device by appropriate connections, and all such configurations are considered to be within the scope of this discussion. Alternatively, the device 10 may be especially-configured for connection to a specified biopsy device. Also illustrated in this figure is a generic connection or interface port 41 to a generic biopsy device, which may serve as a connection to a generic specimen collection chamber 40, and generic vacuum or connection port 42 of a generic specimen collection chamber which may be associated with a generic biopsy device.

According to one embodiment, device 10 may include a detachable structure such as shown in this figure. In such an embodiment, the specimen collection chamber 40 with its luer connection 42 integral to its structure may be connected directly to the vacuum channel 17 by sliding it inside of the specimen chamber aperture tight
of FIG. 1 and as further described in FIG. 3 above. In this embodiment, specimen collection chamber 40 may internally include a screen or tissue capture element configured to trap solid tissue specimens while still allowing liquids to flow through the vacuum pump of device 10 to the fluid and tissue collection chamber of device 10. In this embodiment, element 41 may be thought of as a universal interface block for connection of device 10 to a generic biopsy device. Universal interface block 41 may comprise structures for sealing to specimen collection chamber 41, as well as locking to the specimen collection chamber, and may also comprise structures such as a luer connection or pierce-able seal or other connection structure at its outside or external face for connection to another device such as a generic biopsy device. Elements of this figure, as shown assembled, may thus form a detachable solid tissue specimen collection chamber of device 10. Device 10, in such embodiment, may itself be configured as a complete, universal, self-contained, self-powered external vacuum source with both cytology (liquids) and histology (solid tissue specimens) collection, storage, preservation and transport capabilities. Thus configured, device 10 may be readily adapted for use with any generic biopsy device, whether or not such a generic biopsy device itself has structure for cytology and/or histology collection and/or transport of captured tissue and liquids to a specimen collection chamber.

Figure 6:
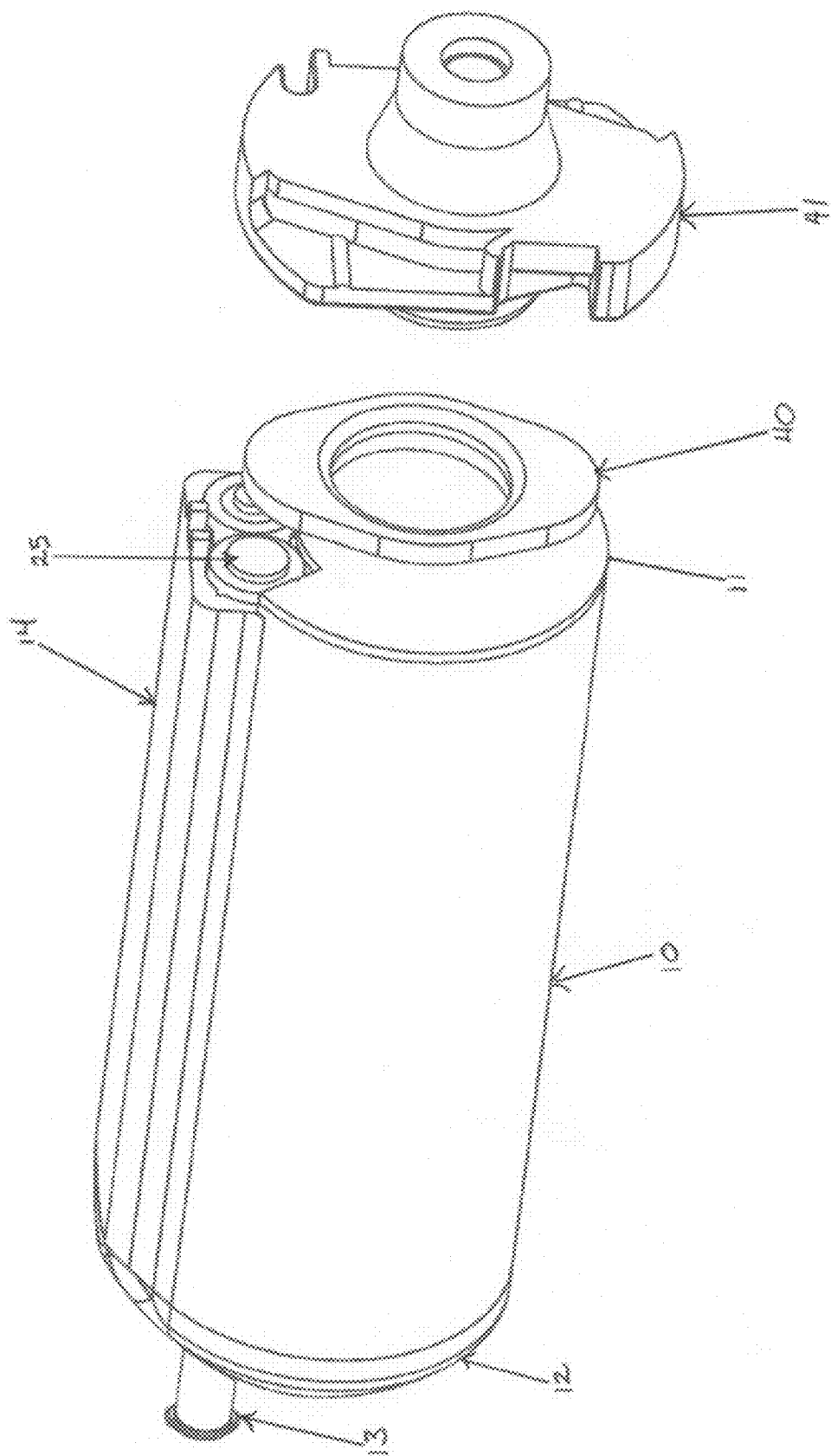
FIG. 6 is an angled side view of a vacuum and cytology collection device 10 placed over a generic specimen collection chamber of a separate, generic biopsy device, according to one embodiment.

FIG. 6 is an angled side view of a device 10 placed over a generic tissue specimen collection chamber 40 of device 10 itself, according to one embodiment, or of a separate, generic biopsy device, according to another embodiment. As discussed above relative to FIG. 5, such a generic specimen collection chamber 40 may be adapted to fit within the aperture 15 formed by device 10's inner wall 21. As also previously discussed above, such a generic specimen collection chamber 40 of a generic biopsy device may be coupled to device 10 by any of a number of connection configurations if such generic specimen collection chamber 40 is not of a size or configuration to fit within device 10. As discussed above for FIG. 5, a generic biopsy device's generic connection port 41 may serve as a port for access to such a device's specimen collection chamber 40. In this illustration, device 10 is shown fully assembled with front plate 11, rear plate 12 with its external exhaust port 13, and a battery and vacuum pump compartment 14 with a battery or batteries 25 inserted in close proximity to a vacuum pump (not visible in this illustration), as well as a universal interface block 41, shown detached from the specimen collection chamber 40, according to embodiments. The specimen collection chamber 40 may be fitted to and seal to such a universal interface block 41, both of which may be considered elements of device 10, or may serve as a connection to a generic biopsy device, according to embodiments. Not shown in this figure is an internal screen mechanism for specimen collection chamber 40, configured to separate solid tissue specimens from liquids and to maintain such solid tissue specimens within the specimen collection chamber 40 while allowing the liquids to pass to the vacuum pump of device 10. In such an embodiment, device 10 is a universal, self-contained, self-powered, external vacuum source and both cytology and histology collection, storage, preservation and transport device for use with any generic biopsy device.

Figure 7:
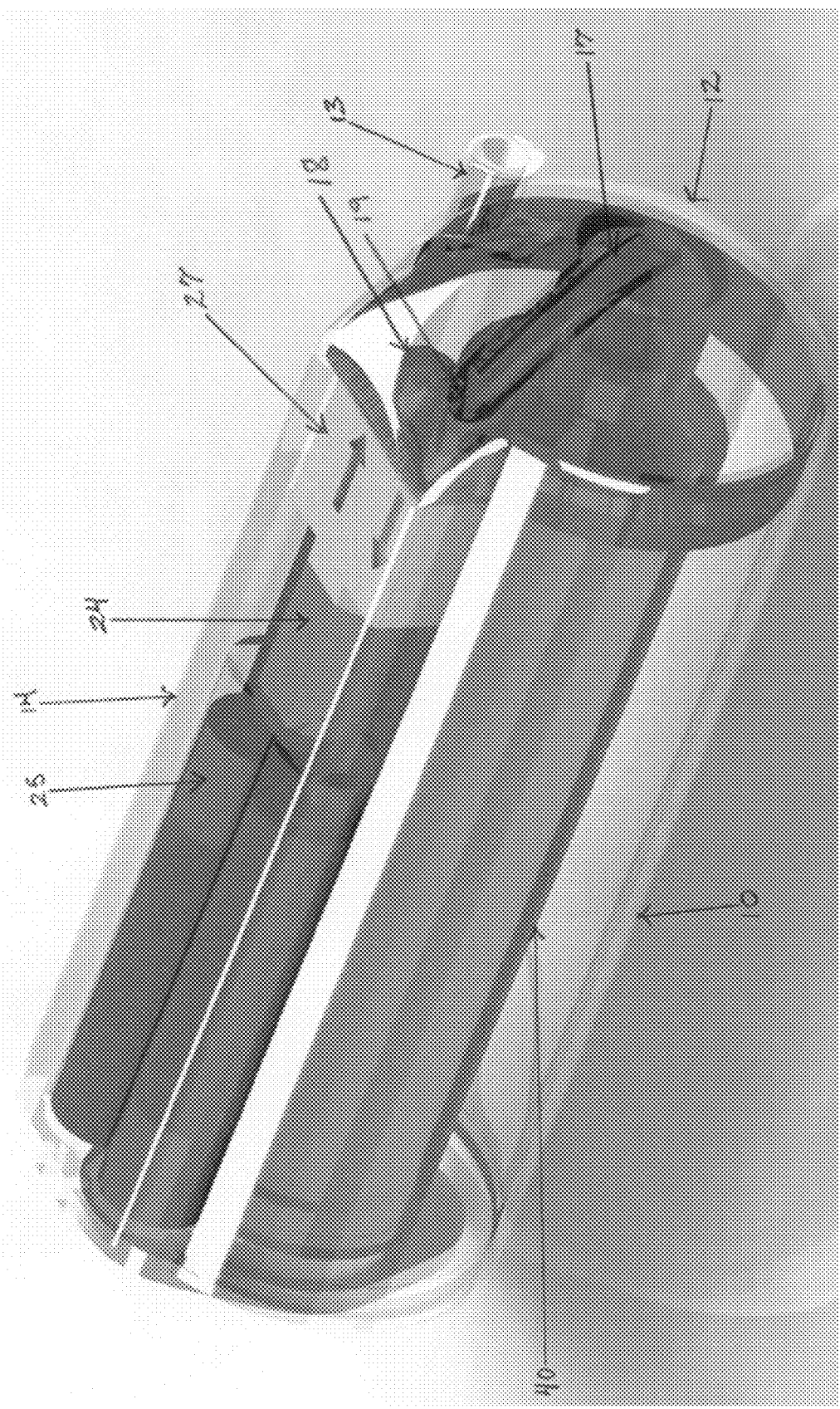
FIG. 7 is an angled, transparent, rear view of a vacuum and cytology collection device 10, placed over a generic specimen collection chamber of a separate, generic biopsy device, according to one embodiment.

FIG. 7 is an angled, transparent, rear view of a vacuum and cytology collection device 10, placed over device 10's integral, detachable specimen collection chamber 40, or alternatively over a generic specimen collection chamber 40 of a separate, generic biopsy device (not shown in this illustration), according to embodiments. In this illustration, a specimen collection chamber 40 of device 10 itself or of a generic biopsy device may be seen, with its discharge connected to vacuum port 17 of rear plate 12 to the right side of the illustration. Also visible in this illustration is battery or batteries 25 and integral vacuum pump 24 within the battery and vacuum pump compartment 14 of device 10, according to embodiments. For illustrative purposes, device 10's vacuum pump interface block 27 may also be seen through a transparent battery and vacuum pump compartment 14, with corresponding embossed arrows referencing intake and exhaust connections between the vacuum pump 24 and interface block 27, according to one embodiment. It may be seen that the arrow on interface block 27 pointing toward vacuum pump 24 also corresponds to vacuum channel 17 through vacuum port 19 of rear plate 12, and thus it may be easily envisioned that the vacuum pump 24 may draw vacuum directly from generic specimen collection chamber 40 and that air or liquids may be discharged from vacuum pump 24 through interface block 27 with its exhaust port 18 to the cytology collection chamber between inner wall 21 and outer wall 20 of device 10, according to methods and embodiments. External exhaust port 13 of rear plate 12 may also be seen in this illustration, and may be envisioned as an exit port for eventual emptying of the cytology collection chamber of device 10, as discussed above, and according to methods and embodiments herein.

Figure 8:
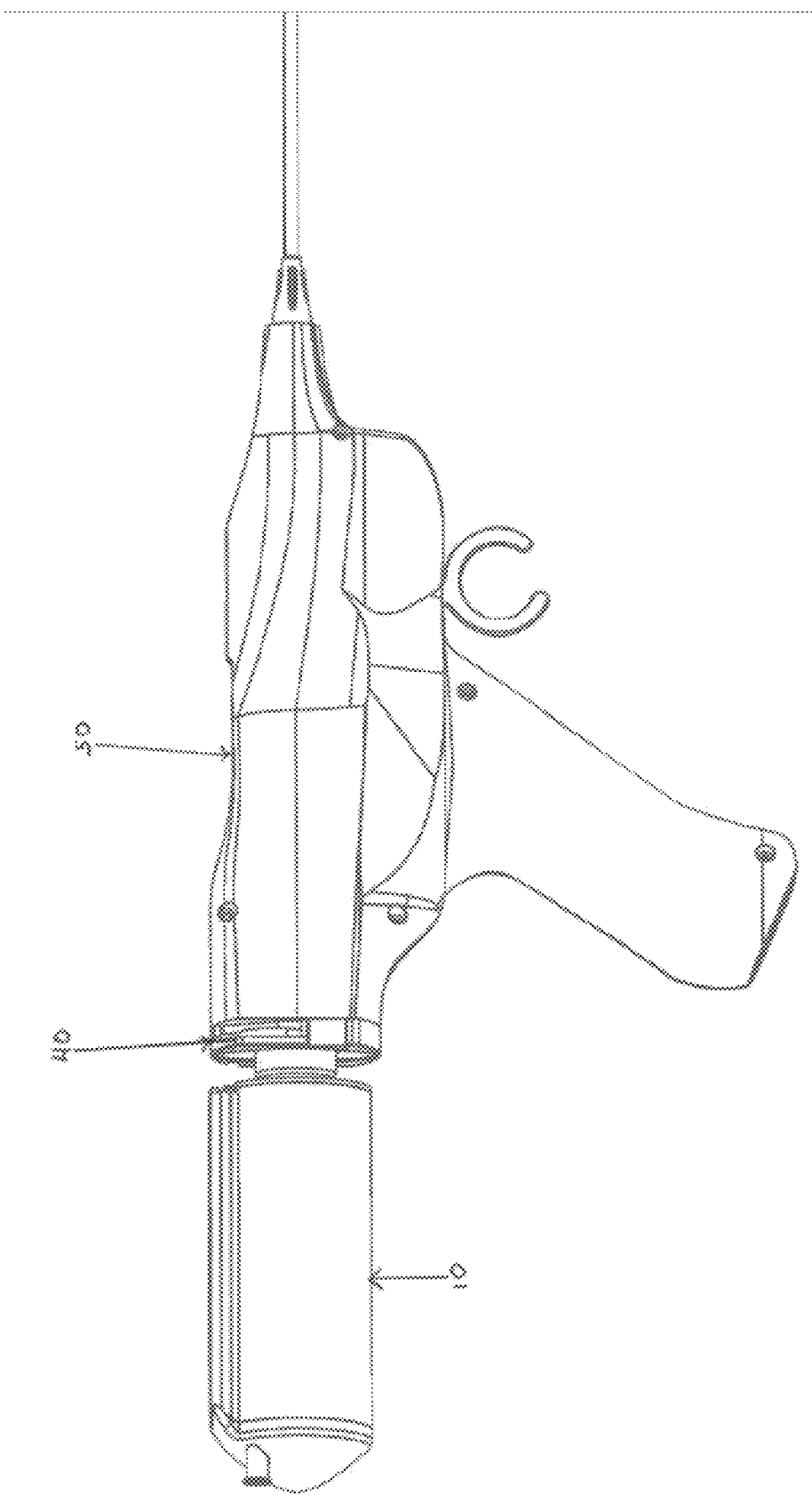
FIG. 8 is a side view of a vacuum and cytology collection device 10 according to one embodiment, placed over the specimen collection chamber of a separate biopsy device.

FIG. 8 is a side view of a vacuum and cytology collection device 10 placed over the specimen collection chamber 40 of a separate, generic biopsy device 50, according to one embodiment. From this illustration, it is to be understood that device 10 has been configured to function as a universal, self-contained, self-powered, compact, portable vacuum source and cytology, or cytology and histology, collection, storage, preservation and transport system for generic biopsy and other interventional medical device instruments, as may be desired and to which it may be adapted, according to methods and embodiments herein.

It is to be understood that any foregoing dimensions discussed and indeed any dimensions referred to herein are exemplary in nature only. Those of skill in this art will recognize that other dimensions and/or configurations may be implemented, depending upon the application, and that the elements of the device 10 could be of any length or dimension, all of which are considered within the scope of this disclosure. Furthermore, any discussion of dimensions or ranges of dimensions or physical or dynamic aspects such as flow rates or ranges of motion or time factors outlined herein are exemplary in nature only and should not be considered to be limiting.

The entire device 10 may be configured to be disposable or may be configured to be reusable in whole or in part. Embodiments of the present device may be electrically powered by one or more batteries and/or external power sources through a simple electrical coupling to connect to an external power supply conveniently placed, for example, in the handle or proximal end of the present biopsy device. The entire device may also be internally or externally manually powered, mechanically powered or be powered by means such as compressed air, gas, vacuum systems or pressurized fluid. Powering the device entirely mechanically may be advantageous in areas in which the electric grid is absent, unavailable, or unreliable.

One embodiment is a method of carrying out a biopsy or interventional procedure with a generic biopsy device to which device 10 described herein is attached. Device 10 may be connected to such a generic biopsy device directly or via a connection system of any appropriate configuration and structure. The device 10 may then power to device 10's vacuum pump to allow vacuum to be applied to the generic biopsy device, along with collection of fluids and cytology as may be discharged from the generic biopsy device to device 10, as discussed above. Device 10 may be exchanged for a spare device 10 intra-operatively, as may be desired by an operator, by simply removing it from its interface connection with a generic biopsy device and replacing the previous device 10 with a spare device 10. Alternatively, device 10's external exhaust port 13 may be used to connect device 10 to an additional vacuum source or containment vessel of larger size than device 10's cytology collection chamber, as may be desired, and according to various methods, all of which are considered to be within the scope of this discussion.

It is to be understood that the above descriptions are but exemplary methodologies and that one or more of the steps described above may be omitted, while other steps may be added thereto to any of these embodiments, depending on the target site within the body. Other operator method embodiments and device embodiments are supported as well. The order of some of the steps may additionally be changed, according to the desired procedure.

The present device may be formed of or comprise one or more biocompatible or other materials such as, for example, stainless steel or other biocompatible alloys, and may be made of, comprise or be coated with polymers, such as polycarbonate, PEEK, tubing, polyimide, and/or biopolymer or other polymer materials as needed to optimize function (s). Some of the components may be purposely surface-treated differentially with respect to adjacent components, as detailed. The various internal or external elements of device 10 may be made of any suitable, commercially available materials such as nylons, polymers such as moldable plastics, and others. If used, the motor or vacuum pump powering the various powered functions of the present vacuum and cytology collection device 10 may be a commercially available electric DC motor. The handle or outer surface of the present device may likewise be made of or comprise inexpensive, injection-molded plastic or other suitable rigid, easily hand held strong and light-weight material. The handle or outer device configuration may be configured in such a way as to make it easily adaptable to or compatible with one of any number of existing guiding platforms, such as stereotactic table stages. The materials used in the present device may also be carefully selected from a ferro-magnetic standpoint, such that the present device maintains compatibility with MRI equipment.

The power source may comprise an external commercially available AC to DC transformer approved for medical device use and plugged into a provided socket in the present biopsy device, or may comprise an enclosed battery or batteries of any suitable and commercially available power source. The battery may be of the one-time use disposable (and optionally recyclable) variety, or may be of the rechargeable variety. Additionally, other power sources, for example, mechanical linkages or compressed air motors, may be used.

While certain embodiments of the disclosure have been described, these embodiments have been presented by way of example only, and are not intended to limit the scope of the disclosure. Indeed, the novel methods, devices and systems described herein may be embodied in a variety of other forms and other applications. All such other applications making use of the principles disclosed herein for this device and that could be envisioned by one skilled in the art are therefore considered to be within the scope of this disclosure. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures and dimensions thereof may differ from those shown in the figures. Depending on the embodiment, certain steps described in the example above may be removed, others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A device, comprising:
   a main body element;
   an inner element co-axially disposed within the main body element and spaced away therefrom, the inner element being configured to receive a specimen collection chamber of an interventional medical device instrument;
   a fluid and tissue collection chamber defined by a space extending at least partially between an inner wall of the main body element and an outer wall of the inner element;
   a vacuum pump comprising an exhaust port, the vacuum pump being attached to the main body element; and
   a sealed vacuum channel configured to provide a vacuum connection between the inner element and the vacuum pump, the vacuum pump being configured to draw at least one of fluid and tissue from the specimen collection chamber through the sealed vacuum channel, out of the exhaust port and into the fluid and tissue collection chamber.

2. The device of claim 1, wherein the vacuum pump is externally powered.

3. The device of claim 1, wherein the vacuum pump is battery-powered.

4. The device of claim 1, wherein the collection device comprises a battery and vacuum pump compartment comprising the vacuum pump and configured to accommodate at least one battery that is configured to power the vacuum pump.

5. The device of claim 4, wherein the battery and vacuum pump compartment is configured to accommodate two batteries side by side.

6. The device of claim 1, further comprising a vacuum pump compartment that is bounded by an extent of the main body element and that is attached to the main body element, the vacuum pump compartment being configured to house the vacuum pump and a power source for the vacuum pump.

7. The device of claim 1, wherein
   the main body element is shaped as a cylinder over at least a portion of its extent;
   the inner element is shaped as a cylinder over at least a portion of its extent; and
   the fluid and tissue collection chamber is shaped as a cylinder over at least a portion of its extent.

8. The device of claim 1, further comprising an interface block configured to lock the specimen collection chamber of the interventional medical device instrument to a first end of the device when the specimen collection chamber is received in the inner element.

9. The device of claim 1, further comprising an interface block configured to radially orient and lock in an orientation the specimen collection chamber of the interventional medical device instrument to a first end of the device when the specimen collection chamber is received in the inner element.

10. The device of claim 1, wherein the sealed vacuum channel is oriented perpendicularly to an axis of the main body element and an axis of the inner element.

11. The device of claim 1, wherein the sealed vacuum channel comprises a first half vacuum channel and wherein the device further comprises:
   a rear plate configured to attach to a second end of the device, and
   a second half vacuum channel that is configured to form the sealed vacuum channel when the rear plate is attached to the second end of the device.

12. The device of claim 1, wherein the sealed vacuum channel comprises one or more spaced apart vacuum channel ports.

13. The device of claim 1, wherein the exhaust port is further configured to enable emptying the fluid and tissue collection chamber and is further configured to be coupled to at least one of an external vacuum source and an external fluid and tissue collection system.

14. A method, comprising:
   providing a collection device comprising a main body element, an inner element co-axially disposed within the main body element and spaced away therefrom, a fluid and tissue collection chamber defined by a space extending at least partially between an inner wall of the main body element and an outer wall of the inner element, a vacuum pump attached to the main body element, and a sealed vacuum channel extending between the inner element and the vacuum pump, the vacuum pump comprising an exhaust port, the inner element being configured to receive a specimen collection chamber of an interventional medical device instrument;
   coupling the collection device to the specimen collection chamber of the interventional medical device instrument; and
   turning the vacuum pump on and drawing at least one of fluid and tissue from the specimen collection chamber of the interventional medical device instrument through the sealed vacuum channel, out of the exhaust port and into the fluid and tissue collection chamber.

15. The method of claim 14, wherein the coupling comprises coupling the collection device to the interventional medical device instrument.

16. The method of claim 14, wherein the coupling comprises inserting the specimen collection chamber of the interventional medical device instrument into the inner element until an aperture of the specimen collection chamber is in fluid communication with the sealed vacuum channel.

17. The method of claim 14, further comprising intra-operatively removing the collection device from the specimen collection chamber of the interventional medical device instrument.

18. The method of claim 17, further comprising providing a duplicate of the provided collection device and wherein the method further comprises intra-operatively coupling the duplicate of the collection device to the specimen collection chamber of the interventional medical device instrument.

19. The method of claim 14, further comprising powering the vacuum pump from an external power source.

20. The method of claim 14, further comprising powering the vacuum pump from a battery.

21. The method of claim 14, wherein the collection device comprises a battery and vacuum pump compartment comprising the vacuum pump and configured to accommodate at least one battery that is configured to power the vacuum pump.

22. The method of claim 14, further comprising connecting the collection device to an external vacuum source.

23. A method, comprising:
   providing a collection device comprising a main body element, an inner element co-axially disposed within the main body element and spaced away therefrom, a fluid and tissue collection chamber defined by a space extending at least partially between an inner wall of the main body element, an outer wall of the inner element and a vacuum pump attached to the main body element, and a battery and vacuum pump compartment comprising the vacuum pump and configured to accommodate at least one battery that is configured to power the vacuum pump, the inner element being configured to receive a specimen collection chamber of an interventional medical device instrument;

coupling the collection device to the specimen collection chamber of the interventional medical device instrument;

turning the vacuum pump on and drawing at least one of fluid and tissue from the specimen collection chamber of the interventional medical device instrument into the fluid and tissue collection chamber of the collection device through a sealed vacuum channel;

removing the collection device with collected fluid and tissue received therein from the interventional medical device instrument; and providing a spare duplicate of the collection device and intra-operatively coupling the spare duplicate of the collection device to the specimen collection chamber of the interventional medical device instrument.

\* \* \* \* \*